United States Patent [19]

van der Schoot

[11] Patent Number: 4,872,564
[45] Date of Patent: Oct. 10, 1989

[54] METHOD OF, AND APPARATUS FOR, AUTOMATICALLY CHECKING EGGS FOR FLAWS AND BLEMISHES, SUCH AS CRACKS, BLOOD, DIRT, A LEAK, ABERRANT FORM AND THE LIKE

[75] Inventor: Jelle van der Schoot, Aalten, Netherlands

[73] Assignee: Staalkat B.V., Netherlands

[21] Appl. No.: 203,102

[22] Filed: Jun. 7, 1988

[30] Foreign Application Priority Data

Jun. 30, 1987 [NL] Netherlands .................. 8701531

[51] Int. Cl.⁴ .................. A01K 43/00; B07C 5/02; B07C 5/342
[52] U.S. Cl. .................. 209/511; 198/387; 209/588; 209/701; 356/57; 356/426
[58] Field of Search .................. 209/510, 511, 563–566, 209/588, 701, 934, 938, 939; 198/779, 387; 356/52, 53, 55–58, 65, 426

[56] References Cited

U.S. PATENT DOCUMENTS

| | | | |
|---|---|---|---|
| 2,849,913 | 9/1958 | Bohlman | 209/511 X |
| 2,872,040 | 2/1959 | Davis | 209/701 X |
| 2,987,182 | 6/1961 | Ator et al. | 209/511 X |
| 3,760,929 | 9/1973 | Lederer | 198/779 X |
| 4,161,366 | 7/1979 | Bol et al. | 356/56 |
| 4,726,898 | 2/1988 | Mills et al. | 209/939 X |
| 4,775,051 | 10/1988 | van der Schoot | 209/510 |

Primary Examiner—Johnny D. Cherry
Assistant Examiner—Edward M. Wacyra
Attorney, Agent, or Firm—Griffin, Branigan & Butler

[57] ABSTRACT

A method of checking eggs for flaws and blemishes, such as blood, dirt, cracks, a leak or aberrant form, in which the eggs, while located on a conveyor roller track, pass an inspection station, where the unwanted eggs are determined as such, with the information of the respective eggs being stored in a tracking memory (shift register), after which the unwanted eggs are discharged separately, whereby more in particular for a fast detection of flaws and blemishes, the eggs for for a short period be lifted off either of two bearing rollers of the conveyor roller track, and brought into contact with other rollers being driven at high peripheral speed, during which period the egg is sensed by a detector, which transmits the result of the sensing to the memory.

4 Claims, 2 Drawing Sheets

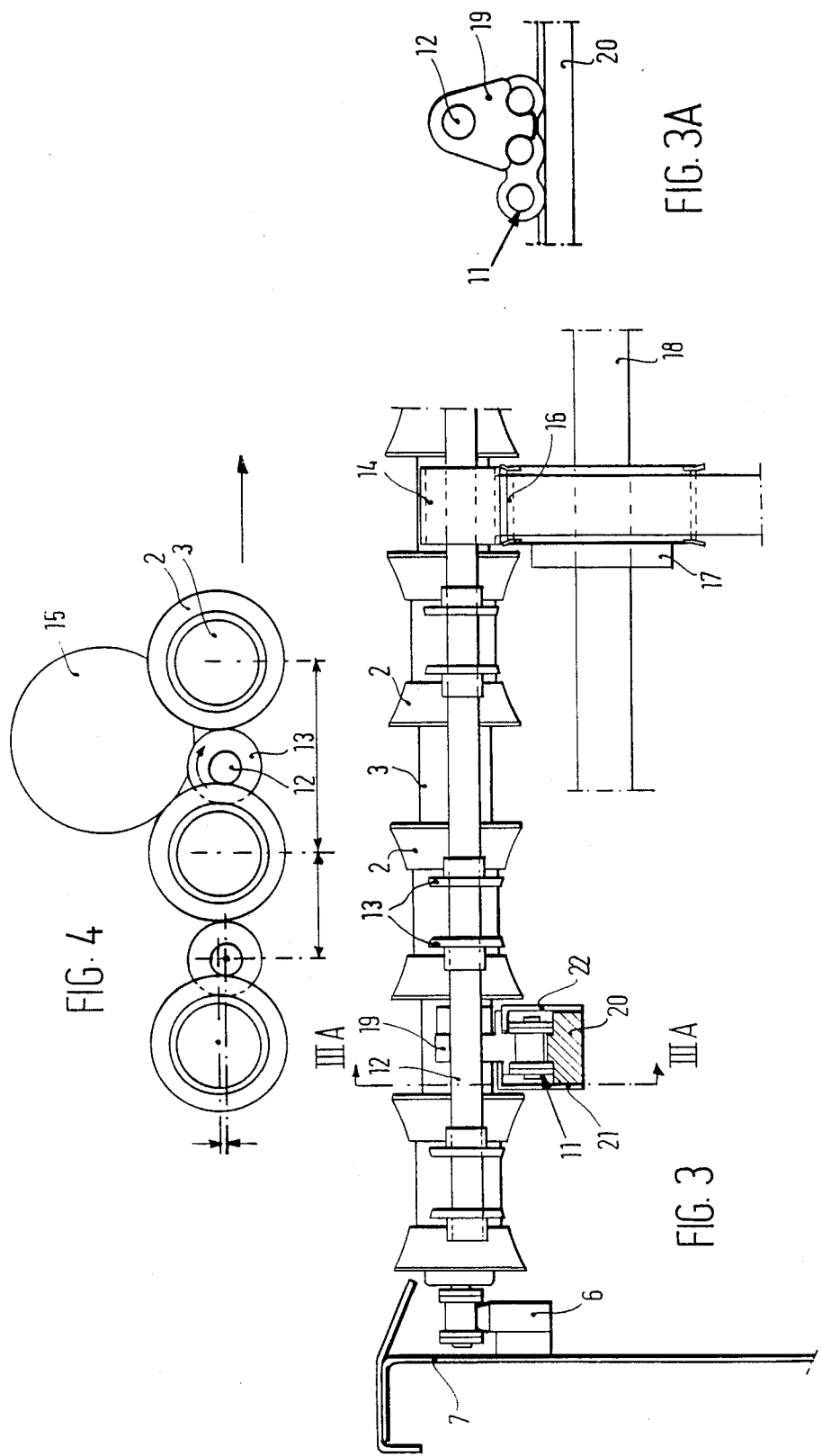

METHOD OF, AND APPARATUS FOR, AUTOMATICALLY CHECKING EGGS FOR FLAWS AND BLEMISHES, SUCH AS CRACKS, BLOOD, DIRT, A LEAK, ABERRANT FORM AND THE LIKE

This invention relates to a method of checking eggs for flaws and blemishes, such as blood, dirt, cracks, a leak, aberrant form or the like, in which the eggs, while located on a conveyor roller track, pass an inspection station, where the unwanted eggs are determined as such, with the information of the respective eggs being stored in a tracking memory (shift register), after which the unwanted eggs are discharged separately.

In an apparatus of this kind, described in Applicants' Dutch Patent Application 84.00080, meanwhile abandoned, and the corresponding U.S. patent application Ser. No. 752,355 dated Mar. 7, 1985, the eggs are checked visually and then touched with a pointer having a switch and an amplifier, said pointer being connected to a tracking memory, after which the eggs, downstream of the light source, are discharged via a trapdoor incorporated in the transporting track.

It is an object of the present invention to achieve an entirely automatic check at high speed.

To that end, the method is characterized in that more in particular for quickly detecting flaws and blemishes, the eggs are for a short period lifted off either of two bearing rollers of the conveyor roller track, and brought into contact with other rollers driven at high peripheral speed and during which period the egg is sensed by a detector, which transmits the result of the sensing to said memory. The eggs are thus not removed from the main conveyor, which not only results in a gain of time but moreover reduces the risk of breakage.

To obtain an effective rotation of an egg during sensing, the peripheral speed of the rollers of the auxiliary roller track is kept higher than the speed at which the eggs are being supplied.

The present invention further relates to an apparatus for performing the above method, which comprises a conveyor roller track, a light source arranged adjacent said track, as well as a detector, as disclosed in the above Dutch application 84.00080.

The apparatus according to the invention is characterized by an auxiliary roller track having smaller rollers than those of the above conveyor roller track, and a part of said auxiliary roller track, in operation, being movable between the rollers of the conveyor roller track in such a manner that, at the position where the rollers of the auxiliary roller track extend between the rollers of the conveyor roller track, the eggs to be transported each rest temporarily on one roller of the conveyor roller track and one roller of the auxiliary roller track.

An additional important advantage of this construction is that in case of breakage, the egg contents are not spread but that only the two coacting rollers, i.e., a conveyor track roller and an auxiliary track roller, are soiled. However, these rollers can be cleaned immediately after removal of the egg in question.

For the sake of completeness, it is observed that Dutch patent application 77.01472, and the corresponding German Pat. No. 2,605,721 disclose a method of automatically checking eggs for cracks or breakage, in which an egg is scanned with a light beam passed over the egg shell and the intensity of the light penetrating into the egg is measured while the egg is being rotated, and in which the light beam is at right angles to the axis of rotation. These publications also describe an apparatus for performing this method. In this known method and apparatus, however, the eggs have to be removed from the transporting track and be placed on a separate apparatus with stationary parts, in contrast to the present invention, in which they are sensed during transport along the conveyor roller track.

In a further elaboration of the invention, the respective rollers of the auxiliary roller track can be positioned eccentrically between the rollers of the conveyor roller track, thereby ensuring that an egg is supported on two similar rollers.

The invention will now be described in more detail with reference to the accompanying drawings, showing, by way of example, one embodiment of an apparatus for checking eggs for flaws and blemishes in accordance with the present invention. In said drawings, FIG. 1 is a diagrammatic side elevational view of a part of an apparatus for checking eggs for flaws and blemishes;

FIG. 3 is an elevational view taken on the line III—III of FIG. 1, with omission of the eggs and of some parts;

FIG. 3A is an elevational view taken on the line IIIA—IIIA of FIG. 3, with omission of the cover; and FIG. 4 is a diagrammatic side view on the basis of which the operation of the apparatus according to the invention will be described.

Figures 1, 2:
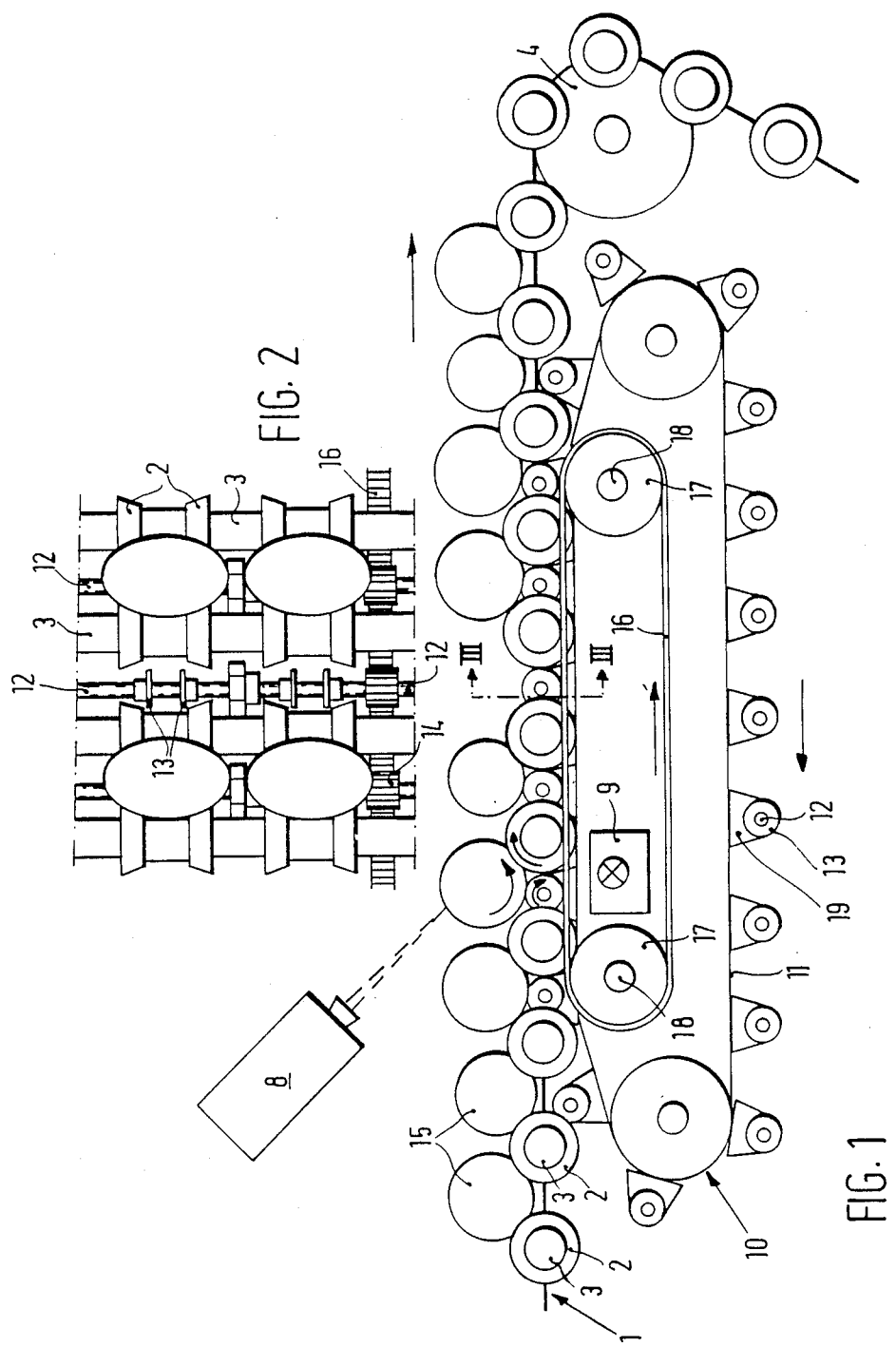
FIG. 2 is a top plan view of a part of the apparatus shown in FIG. 1.

As shown in the drawings, see in particular FIGS. 1 and 2, an apparatus for checking eggs for flaws and blemishes comprises a conveyor roller track 1, shown diagrammatically, having collars 2 mounted on shafts 3. Shafts 3 are interconnected by links, not shown, and thus form the conveyor roller track 1, running on return rollers 4, a single one of which is shown in FIG. 1. One of the other return rollers 4 can be driven. Adjacent the part of the apparatus shown, the shafts are supported laterally by a roller track 6, attached to the wall 7 (see FIG. 3) of a frame, not further shown.

Above the part of the conveyor track shown in FIG. 1, a detector 8 is arranged and a light source 9 is provided underneath the conveyor track. The light which the light source 9 shines in the direction of the egg is sensed by detector 8. To improve this sensing an auxiliary roller track 10 is arranged underneath the respective part of the conveyor track. The auxiliary track consists essentially of chains 11, shown diagrammatically, which are connected by shafts 12 to auxiliary rollers 13 mounted thereon. Shafts 12 are interspaced similarly to shafts 3 of conveyor roller track 1. The upper part of the conveyor chains 11 is guided in the central portion along raised rollers (not shown), which are disposed at such a level that at this position the auxiliary rollers 13 are present between rollers 2 of conveyor roller track 1. The arrangement is such that the articles, i.e. eggs 15, transported by conveyor roller track 1 rest exclusively on one roller 2 and one roller 13. Rollers 13 are driven through pinions 14 mounted on shafts 12 by a toothed belt 16, arranged adjacent said raised portion of conveyor chains 11, said toothed belt being guided over return rollers 17 mounted on shafts 18.

As shown in FIGS. 1 and 3, shafts 12 are mounted on chain 11 by means of one or more bearing brackets 19.

Chain 11 itself is supported by a guide 20. Chain 11 is further protected against fouling through covers 21, 22 attached to guide 20.

In the embodiment described above the rollers of the auxiliary roller track are driven through toothed belts 16, while the rollers of the conveyor roller track are not driven per se but make a rolling movement by contact with a guide or support, not shown. However, this is not essential, as the conveyor rollers can also be driven without any objections. The essential point is that the eggs supplied make a fast turn, with the peripheral speed of the egg being higher than the speed at which the eggs are supplied.

The movements of the various parts during operation is shown in the drawings by arrows.

What I claim is:

1. In a method for inspecting eggs for flaws or blemishes wherein eggs are placed on a conveyor roller track having two conveyor rollers for supporting each egg, passing the eggs by an inspection means for generating information as to which eggs have flaws or blemishes and storing said information in a tracking memory for subsequently discarding flawed or blemished eggs, the improvement comprising temporarily interdisposing an auxiliary roller of an auxiliary roller track between the said two conveyor rollers such that the egg supported thereby is temporarily supported by a first of said two conveyor rollers and said interdisposed auxiliary roller and lifted off of the second of the said two conveyor rollers, causing the said interdisposed auxiliary roller to rotate at a greater peripheral speed than that of the said first conveyor roller to impart such rotation to the egg so as to increase the speed of inspection thereof by said inspection means as the said rotating egg passes thereby.

2. A method as claimed in claim 1, wherein the peripheral speed of the auxiliary roller is greater than the peripheral speed at which the eggs are supplied.

3. In an apparatus for inspecting eggs for flaws or blemishes having a conveyor roller track for conveying eggs with adjacent conveyor rollers thereof adapted to receive a single egg, a light source disposed adjacent the conveyor roller track, a light detector for generating information as to which eggs have flaws or blemishes and storage means for storing said information in a tracking memory for subsequently discarding flawed or blemished eggs, the improvement comprising an auxiliary roller track having a plurality of auxiliary rollers, means for temporarily interdisposing an auxiliary roller between said adjacent conveyor rollers such that the egg supported thereby is temporarily supported by a first of said conveyor rollers and the interdisposed auxiliary roller and lifted off of the second of the adjacent conveyor rollers, means for causing the interdisposed auxiliary roller to rotate at a greater peripheral speed than that of the first of said conveyor rollers to impart such rotation to the egg so as to increase the speed of inspection thereof by said detector as the said rotating egg passes thereby.

4. An apparatus as claimed in claim 3, wherein the auxiliary rollers are disposed eccentrically between the adjacent conveyor rollers such that the axis of an auxiliary roller is closer to the axis of one of the adjacent conveyor rollers than to the other.

* * * * *